{| | |}
United States Patent [19]

Sulkowski et al.

[11] 4,365,063

[45] * Dec. 21, 1982

[54] ANTIHYPERTENSIVE AGENTS

[75] Inventors: Theodore S. Sulkowski, Wayne; James L. Bergey, Lansdale; Albert A. Mascitti, Norristown, all of Pa.

[73] Assignee: American Home Products Corporation, New York, N.Y.

[ * ] Notice: The portion of the term of this patent subsequent to Mar. 23, 1999, has been disclaimed.

[21] Appl. No.: 297,645

[22] Filed: Aug. 31, 1981

[51] Int. Cl.³ .................................... C07D 471/02
[52] U.S. Cl. .................................. 546/123; 544/127; 544/362; 424/248.55; 424/250; 424/256
[58] Field of Search ............... 546/122, 123; 544/127, 544/362

[56] References Cited

U.S. PATENT DOCUMENTS

| | | | |
|---|---|---|---|
| 3,271,441 | 9/1966 | Brace | 546/122 |
| 3,325,505 | 6/1967 | Loev | 260/295.5 |
| 3,429,887 | 2/1969 | Lesher | 260/294.9 |
| 3,441,648 | 4/1969 | Loev et al. | 424/263 |
| 3,773,773 | 11/1973 | Bossert | 260/294.8 |
| 3,799,934 | 3/1974 | Meyer et al. | 260/294.8 |
| 4,022,898 | 5/1977 | Meyer et al. | 424/251 |
| 4,038,399 | 7/1977 | Bossert et al. | 424/266 |
| 4,177,278 | 12/1979 | Bossert et al. | 424/266 |
| 4,321,384 | 3/1982 | Sulkowski et al. | 546/123 |

FOREIGN PATENT DOCUMENTS 843576  6/1976  Belgium .

OTHER PUBLICATIONS

J. Med. Chem., 17, No. 9, 956 (1974).
Arzneim–Forsch, 22, 22 (1972).
Arch. Pharmacol., 310, 69 (1979).
C.A.: 59:2823b and CA 59:3823b.

*Primary Examiner*—Ethel G. Love
*Attorney, Agent, or Firm*—Richard K. Jackson

[57] ABSTRACT

1,4,5,6,7,8-Hexahydro-2-alkyl-4-pentafluorophenyl-5-oxo-1,7-naphthyridine-3-carboxylic acid esters and pharmaceutically acceptable salts thereof are useful antihypertensive agents.

4 Claims, No Drawings

ANTIHYPERTENSIVE AGENTS

BACKGROUND OF THE INVENTION

Pharmacological agents possessing the ability to block cellular transmembrane influx of calcium are capable of suppressing that porton of myocardial or smooth muscle contractility which is dependent upon extracellular calcium. These pharmacological agents, termed calcium antagonists, have been proven to be useful in the treatment of hypertension, cardiac arrhythmias, angina pectoris, cardiac myopathy and coronary artery vasospasm (a possible cause of sudden cardiac death syndrome). Can J. Physiol. Pharmacol., 57 443 (1979); Drugs, 15 169 (1978); Acta Pharmacol. Toxicol., 43, suppl. 1, 45 (1978).

In theory, calcium antagonists are thought to act by blocking calcium influx through discrete calcium channels (slow channels) in cell membranes. Various tissues exhibit relative differences in sensitivity toward the calcium blocking effect achieved by certain calcium antagonists, theoretically as a result of tissue specific differences in the calcium channels. Acta Pharmacol. Toxicol., 43, 5, (1978); loc. cit. 291 (1978); Microvascular Res., 5 73 (1973); Am. Rev. Pharmacol. Toxicol., 17 149 (1977). Calcium channels of tissues which are most sensitive to calcium antagonist blockade are those which allow calcium influx only when the cell membranes are electrically depolarized. α-adrenergic receptor-activated calcium channels are relatively unaffected by these agents. Circ. Res., 46 426 (1980). This observation provides basis for evaluation of calcium antagonism.

Thus, vascular smooth muscle tissue from the rabbit aorta can be made to contract when exposed to a depolarizing solution containing an elevated potassium ion concentration and normal amounts of calcium ions. Calcium antagonists added to the solution produce a dose dependent relaxation of the contracted rabbit aortic tissue. Normal contraction of the aortic tissue can then be induced in the presence of a calcium antagonist by subsequent addition of an α-adrenergic agonist, such as norepinephrine, to the solution. Eur. J. Pharmacol., 53 281 (1979); Circ. Res., 46 426 (1980); J. Exp. Pharmacol. Therap., 174 500 (1970). The normal contraction produced by an α-adrenergic agonist after maximal smooth muscle relaxation has been induced by a calcium antagonist, serves to distinguish the calcium blocking effect of an agent from a nonspecific depressant effect on the muscle.

DESCRIPTION OF THE INVENTION

In accordance with this invention there is provided a group of 1,4,5,6,7,8-hexahydro-2-alkyl-4-pentafluorophenyl-5-oxo-1,7-naphthyridine-3-carboxylic acid esters and pharmaceutically acceptable salts thereof, which compounds are calcium antagonists useful in the treatment of hypertension.

More specifically, the antihypertensive agents of this invention are compounds of the formula:

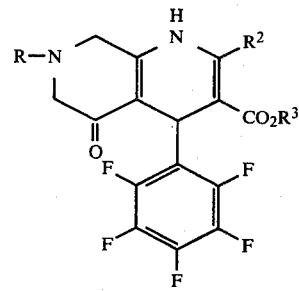

in which

R is hydrogen, alkyl of 1 to 6 carbon atoms or benzyl;

$R^2$ is alkyl of 1 to 6 carbon atoms; and $R^3$ is alkyl of 1 to 6 carbon atoms; alkoxyalkyl in which each alkyl moiety has 1 to 6 carbon atoms, $-CH_2CF_3$, $-CH_2CH_2CF_3$ or

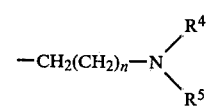

where $R^4$ is hydrogen or alkyl of 1 to 6 carbon atoms; and $R^5$ is alkyl of 1 to 6 carbon atoms or arylalkyl of 7 to 10 carbon atoms and $R^4$ and $R^5$ taken with the nitrogen atom to which they are attached form a pyrrolidinyl, imidazolidinyl, piperidyl, piperazinyl, 4-alkyl-piperazinyl in which the alkyl group contains from 1 to 6 carbon atoms or morpholinyl heterocycle;

or a pharmaceutically acceptable salt thereof.

With reference to the above described genus of compounds, the preferred variables, from the standpoint of production economics and availability of starting materials, are those in which the aliphatic moieties are straight or branched chain containing from 1 to 4 carbon atoms, the arylalkyl group representing $R^5$ os benzyl or phenethyl and n is 1 or 2.

The compounds of this invention are prepared by reaction of equimolar amounts of 3-oxo-5-hydroxy-1,2,3,6-tetrahydropyridine derivatives (piperidine-3,5-diones), an aldehyde and a 3-aminocrotonate derivative, thusly:

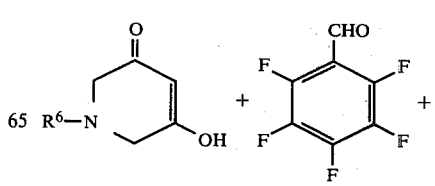

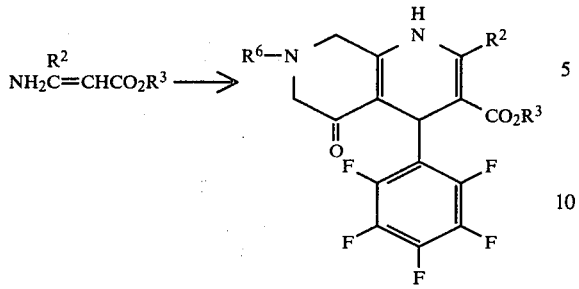 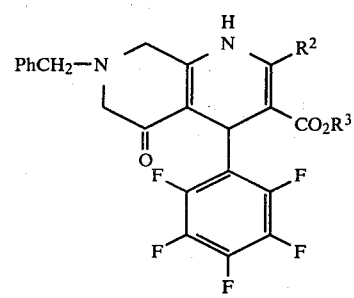

where $R^6$ is alkyl of 1 to 6 carbon atoms or benzyl. The benzyl group is removed by hydrogenolysis to afford the 7-unsubstituted products.

The aminoalkyl esters may be prepared by formation of the substituted aminocrotonate in situ via ammonolysis of the desired aminoalkyl acetoacetic acid ester.

The 3-oxo-5-hydroxy-1,2,3,6-tetrahydropyridines used as starting materials are prepared from N-substituted glycine used by standard procedures. The N-methyl and N-benzyl 3-oxo-5-hydroxy-1,2,3,6-tetrahydropyridines are literature compounds. Archiv. der Pharmazie, 300 91 (1967); J.A.C.S. 95 7458 (1973); Tet. Lett., 4075 (1977). The preparatory technique generally follows the equations:

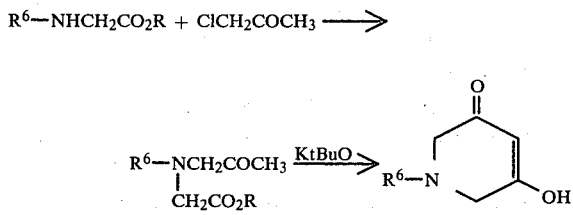

The aldehyde and amino crotonate reactants are either commercially available or may be prepared by standard procedures.

The pharmaceutically acceptable salts of the antihypertensive agents of this invention are prepared directly by neutralization of the free base or by metathetical displacement. The physiologically acceptable salts may be formed with organic or inorganic acids such as hydrochloric, hydrobromic, phosphoric, sulfuric, sulfonic, nitric, methylsulfonic, acetic, maleic, succinic, fumaric, tartaric, citric, salicylic, lactic, naphthalenedisulfonic acid, and the like.

The N-benzyl 1,4,5,6,7,8-hexahydro-2-alkyl-4-aryl-5-oxo-1,7naphthyridine-3-carboxylic acid esters form an additional intermediate compound aspect of the invention useful in the preparation of the N-unsubstituted analogues referred to supra. The N-benzyl intermediates are depicted by the structural formula:

where $PhCH_2$ is benzyl and the $R^2$ and $R^3$ groups are defined supra. These compounds, although categorized as intermediates herein, are very potent in vitro $Ca^{+2}$ antagonists generally lacking sufficient bioavailability in vivo (because of their insolubility, protein binding propensity or analogous functional deactivating property) to qualify as antihypertensive agents. Derivitization of the 7-benzyl intermediates to afford good in vivo antihypertensive activity is achieved by functionalizing the compounds to provide solubility and avoid physical deactivation in the animal. Thus, the aminoalkyl esters illustrate one method for improving the bioavailability of the 7-benzyl derivatives such that they afford excellent antihypertensive agents without removal of the 7-benzyl substituent. The in vitro $Ca^{+2}$ antagonist activity level and the in vivo blood pressure reduction obtained with these intermediates, is presented in Example 2.

The compounds of this invention were initially shown to exhibit $Ca^{+2}$ antagonism in rabbit aortic strips wherein the strips were contracted in an organ bath containing a modified physiological salt solution (Broekaert et al., Europ. J. Pharmacol. 53 281 (1979)) in which 100 millimoles potassium ion had been substituted on an equimolar basis for sodium ion. After a stable active tension has developed in the strip, as measured by Statham UC-2 force transducers and recorded on an eight channel Beckman Dynograph Polygraphic Recorder, an amount of the antagonist was added to the organ bath to make a $10^{-5}$ molar concentration of antagonist. The depressant effect, expressed as percent relaxation, was taken from the mean of at least two experiments. After maximum $Ca^{+2}$ antagonist induced relaxation was obtained, a maximal dose of norepinephrine ($10^{-5}$ moles) was added to the organ bath to determine whether normal α-adrenergic responses were still effected and show that the compound being tested was not a general depressant. A $Ca^{+2}$ antagonist producing a 20 percent relaxation of aortic tissue in this test procedure at a $10^{-5}$ molar bath concentration of the antagonist, generally produced a significant reduction in blood pressure when a sufficient amount is given to the spontaneously hypertensive rat.

The in vivo blood pressure lowering ability of the compounds of this invention was established by measuring the systolic pressure of spontaneously hypertensive rats with a Decker Caudal Plethysmograph or similar sensor device. The compound being tested is administered to groups of four rats and their blood pressure is read prior to compound administration and at 1.5 and 4 hours after compound administration. Depending upon the behavior of the compound being tested, the schedule of blood pressure readings and route of administration is modified. Initially the compounds are administered orally but where compound solubility is a factor, the compounds may be administered parenterally (i.e. i.p., i.m., s.c., i.v., etc.) as desired. The compounds of this invention were initially administered orally at a standard testing dose of 50 mg/kg., and where appropriate, smaller doses were administered to obtain a potency profile.

Based upon the potency profile elicited by the compounds of this invention in the above-described standard scientifically recognized test models, the compounds are established as hypotensive agents useful in the treatment of hypertension and conditions characterized by constrictive blood flow in coronary arteries. For that purpose, the compounds may be administered orally or parenterally in suitable dosage fors compatable with the route of administration, whether oral, intraperitoneal, intramuscular, intravenous, intranasal, buccal, etc. The effective does range determined in the animal test models has been established at from 1 to about 50 milligrams per kilogram host body weight to be administered in single or plural doses as needed to obtain the desired hypotensive responses. The specific dosage regimen for a given patient will depend upon age, pathological state, severity of dysfunction, size of the patient, etc. Oral administration is performed with either a liquid or solid dosage unit in any conventional form such as tablets, capsules, solutions, etc., which comprise a unit dose (e.g. from about 25 milligrams to about 4 grams) of the active ingredient alone or in combination with adjuvants needed for conventional coating, tableting, solubilizing, flavor or coloring. Parenteral administration with liquid unit dosage forms may be via sterile solutions or suspensions in aqueous or oleagenous medium. Isotonic aqueous vehicle for injection is preferred with or without stabilizers, preservatives and emulsifiers.

The following examples illustrate the preparation of a representative number of compounds of this invention. After each example, the Ca$^{+2}$ antagonist activity of the compound is presented in terms of percent relaxation (P.R.) at the stated concentration. Similarly, the antihypertensive activity is reported in terms of millimeters mercury (mmHg) blood pressure (B.P.) reduction at the stated time post oral dosing with the reported amount of compound.

EXAMPLE 1

1,4,5,6,7,8-Hexahydro-2,7-dimethyl-4-[2,3,4,5,6-pentafluorophenyl]-5-oxo-1,7-naphthyridine-3-carboxylic Acid Methyl Ester 1-Methyl-3-oxo-5-hydroxy-1,2,3,6-tetrahydropyridine (6.36 g.), 5.92 g. of methyl-3-aminocrotonate, 9.8 g. of pentafluorobenzaldehyde and 125 ml. of methanol were refluxed for 4 hours. The reaction mixture was filtered and the filtrate was evaporated to dryness in vacuo. The residue was slurried with ethanol and filtered. Recrystallization from methanol afforded the title compound; m.p. 250°–253° C. dec.

Analysis for: $C_{18}H_{15}N_2F_5O_3$: Calculated: C, 53.74; H, 3.76; N, 6.96; Found: C, 53.42; H, 4.02; N, 6.85

Hydrochloride, m.p. 240°–243° C. dec. (recrystallized from methanol).

Analysis for: $C_{18}H_{15}N_2F_5O_3.HCl$:
Calculated: C, 49.27; H, 3.68; N, 6.38; Cl, 8.08; Found: C, 49.12; H, 3.59; N, 6.38; Cl, 8.07

P.R.=22.9 ($10^{-5}$ M)

B.P.=50 mg/kg −95 at 1.5 hours; −89 at 4 hours.

25 mg/kg −71 at 1.5 hours; −49 at 4 hours.
10 mg/kg −63 at 1.5 hours; −31 at 4 hours.
5 mg/kg −21 at 1.5 hours; −10 at 4 hours.

EXAMPLE 2

1,4,5,6,7,8-Hexahydro-2-methyl-5-oxo-4-(2,3,4,5,6-pentafluorophenyl)-7-(phenylmethyl)-1,7-naphthyridine-3-carboxylic Acid Methyl Ester A mixture of 10.2 g. of 1-benzyl-3-oxo-5-hydroxy-1,2,3,6-tetrahydropyridine, 5.93 g. of methyl-3-aminocrotonate, 10 g. of pentafluorobenzaldehyde and 125 ml. of methanol was refluxed for 4 hours. The solution was allowed to cool to room temperature. The solid was separated by filtration. The solid, m.p. 258°–260° C. dec., was suspended in methanol and saturated with hydrogen chloride. The solution was evaporated to dryness in vacuo. Recrystallization of the residue from methanol afforded the title compound as the hydrochloride, m.p. 198°–200° C. dec.

Analysis for: $C_{24}H_{19}N_2F_5O_3.HCl$: Calculated: C, 55.97; H, 3.91; N, 5.44; Cl, 6.88; Found: C, 55.53; H, 4.12; N, 5.30; Cl, 7.08

P.R.=56 ($10^{-6}$ M)

B.P.=50 mg/kg −20 at 1.5 hours; −23 at 4 hours.

EXAMPLE 3

1,4,5,6,7,8-Hexahydro-2-methyl-5-oxo-4-(2,3,4,5,6-pentafluorophenyl)-1,7-naphthyridine-3-carboxylic Acid Methyl Ester Six grams of 1,4,5,6,7,8-hexahydro-2-methyl-5-oxo-4-(2,3,4,5,6-pentafluorophenyl)-7-(phenylmethyl)-1,7-naphthyridine-3-carboxylic acid methyl ester hydrochloride (Example 2), 200 ml. of methanol, 15 ml. of water and 0.5 g. of 10% palladium on carbon were shaken with hydrogen at an initial pressure of 50 psi. After 3 hours, the catalyst was separated and the filtrate was evaporated to dryness in vacuo. The residue was slurried with ethanol and filtered. Recrystallization from methanol-diethyl ether afforded the title compound as the hydrochloride, m.p. 268°–270° C. dec.

Analysis for: $C_{17}H_{13}N_2F_5O_3.HCl$: Calculated: C, 48.07; H, 3.32; N, 6.59; Cl, 8.34; Found: C, 48.36; H, 3.53; N 6.69; Cl, 7.94

P.R.=65.2 ($10^{-6}$ M); 78.7 ($10^{-5}$ M).

B.P.=50 mg/kg −64 at 1.5 hours; −88 at 4 hours.
25 mg/kg −76 at 1.5 hours
10 mg/kg −79 at 1.5 hours; −24 at 4 hours.
5 mg/kg −48 at 1.5 hours; −36 at 4 hours.
2.5 mg/kg −34 at 1.5 hours; −30 at 4 hours.

What is claimed is:

1. A compound of the formula:

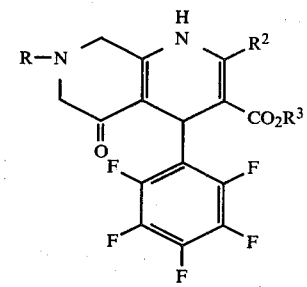

in which

R is hydrogen, alkyl of 1 to 6 carbon atoms or benzyl;

$R^2$ is alkyl of 1 to 6 carbon atoms;
and
$R^3$ is alkyl of 1 to 6 carbon atoms, alkoxyalkyl in which each alkyl moiety has 1 to 6 carbon atoms, —CH$_2$CF$_3$, —CH$_2$CH$_2$CF$_3$ or

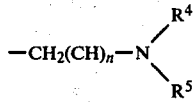

where $R^4$ is hydrogen or alkyl of 1 to 6 carbon atoms and $R^5$ is alkyl of 1 to 6 carbon atoms or arylalkyl of 7 to 10 carbon atoms and $R^4$ and $R^5$ taken with the nitrogen atom to which they are attached form a pyrrolidinyl, imidazolidinyl, piperidinyl, piperazinyl, 4-alkylpiperazinyl in which the alkyl group contains from 1 to 6 carbon atoms or morpholinyl heterocycle, and n is one of the integers 0, 1 or 2;
or a pharmaceutically acceptable salt thereof.

2. The compound which is 1,4,5,6,7,8-hexahydro-2,7-dimethyl-4-(2,3,4,5,6-pentafluorophenyl)-5-oxo-1,7-naphthyridine-3-carboxlyic acid methyl ester.

3. The compound which is 1,4,5,6,7,8-hexahydro-2-methyl-5-oxo-4-(2,3,4,5,6-pentafluorophenyl)-7-phenylmethyl-1,7-naphthyridine-3-carboxylic acid methyl ester.

4. The compound which is 1,4,5,6,7,8-hexahydro-2-methyl-5-oxo-4-(2,3,4,5,6-pentafluorophenyl)-1,7-naphthyridine-3-carboxylic acid methyl ester.

* * * * *